United States Patent
Hutson et al.

(10) Patent No.: US 6,332,467 B1
(45) Date of Patent: Dec. 25, 2001

(54) FEEDING TUBE SPIKE SET WITH INTEGRATED Y-PORT

(75) Inventors: Lonnie Hutson; Leonard Hoffstetter, both of San Dimas; Raymond D. Clark, Oceanside, all of CA (US)

(73) Assignee: LH Medical Products, Inc., San Dimas, CA (US)

( * ) Notice: Subject to any disclaimer, the term of this patent is extended or adjusted under 35 U.S.C. 154(b) by 0 days.

(21) Appl. No.: 09/543,126

(22) Filed: Apr. 5, 2000

(51) Int. Cl.[7] ........................................ A61F 5/37
(52) U.S. Cl. ................. 128/877; 604/80; 604/81
(58) Field of Search ................. 604/80, 81, 82, 604/83, 85, 254; 128/877

(56) References Cited

U.S. PATENT DOCUMENTS

| | | | |
|---|---|---|---|
| 4,705,505 | * 11/1987 | Fried | 604/80 |
| 5,059,173 | * 10/1991 | Sacco | 604/80 |
| 5,160,320 | * 11/1992 | Yum | 604/80 |
| 5,242,392 | * 9/1993 | Vaughn | 604/80 |
| 5,322,073 | * 6/1994 | Michels | 128/876 |

* cited by examiner

Primary Examiner—Michael A. Brown
(74) Attorney, Agent, or Firm—Steins & Associates

(57) ABSTRACT

A Feeding tube spike set with integrated Y-port is disclosed. The preferred spike set includes a spike, a drip chamber, a y-port fitting, a stepped connector, and tubing connecting these components to one another in series. The y-port fitting further includes a body, a plug assembly and an undulating retaining member connecting the plug assembly to the body. The plug assembly further includes a plug from which a pair of tabs extend. The body also includes a flushing port formed within it; the preferred flushing port includes a plurality of ridges formed along it's bore to assist in retaining a secure seal between the inserted plug and the body.

12 Claims, 7 Drawing Sheets

FEEDING TUBE SPIKE SET WITH INTEGRATED Y-PORT

BACKGROUND OF THE INVENTION

1. Field of the Invention

This invention relates to products to permit the enteral feeding of patients, and in particular to an improved feeding tube spike set with integrated Y-port.

2. Description of Related Art

There are two problems associated with enteral patient feeding. The first problem is the inadvertent disconnection of the tubing leading to the feeding tube, the other involves the difficulty of administering water to the patient. The solution provided by previous inventors, namely Michels et al. U.S. Pat. No. 5,322,073 and D360,030, involved providing a y-tube connector that included an integrated retaining strap for the disconnectable tubing entering the connector from the nutrient container. The problem with this arrangement is that the user is required to unplug the entrance to the y-tube and then connect the hose into the y-tube through this cumbersome retaining strap. What would be better would be to simply provide an integrated system that includes all components necessary from the nutrient supply to the enteral connector.

The second problem involves the y-port fitting in the spike set. This y-port fitting is provided to enable health care personal to inject water to either flush the system or to hydrate the patient. The difficulty involves the fact that there are a variety of different means by which the water is introduced into the y-port connector. Many times a variety of different sizes of syringes might be used. In many cases however, the tip of the syringe does not exactly match the configuration of the port in the y-port fitting. What would be very beneficial would be to provide a y-port fitting that permits a wide variety of syringe configurations to be inserted into the fitting, and sealing the syringe tip connection to prevent leakage of water or other material when the patients being hydrated.

SUMMARY OF THE INVENTION

In light of the aforementioned problems associated with the prior devices, it is an object of the present invention to provide a Feeding tube spike set with integrated Y-port. The preferred spike set will include a spike, a drip chamber, a y-port fitting, a stepped connector, and tubing connecting these components to one another in series. It is a further object that the y-port fitting include a body, a plug assembly and an undulating retaining member connecting the plug assembly to the body. It is yet another object that the plug assembly include a plug from which a pair of tabs extend. It is another object that the body include a flushing port formed within it; the preferred flushing port should include a plurality of ridges formed along it's bore to assist in retaining a secure seal between the inserted plug and the body.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a Feeding tube spike set with integrated Y-port.

Figure 1:
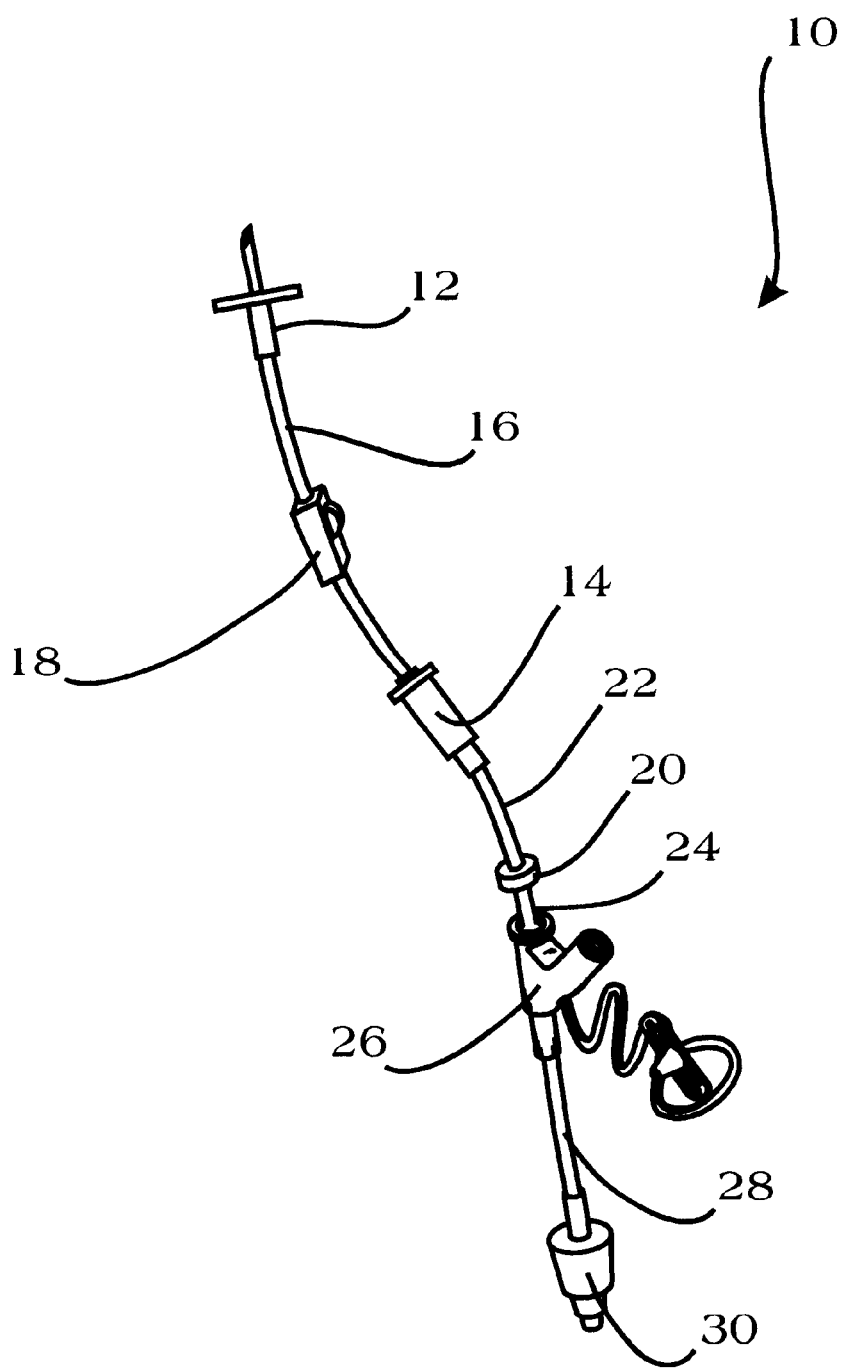
FIG. 1 depicts a preferred embodiment of the improved feeding tube spike set of the present invention.

If we first turn to FIG. 1, we can discuss the improved feeding spike set 10 of the present invention. FIG. 1 depicts a preferred embodiment of the improved feeding tube spike set of the present invention. It should be understood that all components are integrated into a single system to prevent leakage and inadvertent disconnection. The same components as with a conventional system are provided, however, they are permanently attached in string. As such, the system 10 includes a spike 12 which is attached to a drip chamber 14 by a first tube section 16. In between the spike 12 and the drip chamber 14 is found a roller clamp 18 for regulating the flow of nutrients into the patient. The drip chamber 14 then may be attached to a coupling 20 by a second tube section 22. It should be understood that the coupling 20 may or may not be eliminated in other embodiments of spike set 10, depending upon the particular application for the set 10. A third tube section 24 then connects the coupling 20 to the improved y-port fitting 26. A fourth tube section 28 then connects the y-port fitting 26 to a stepped connector 30, which is configured attach to the enteral feeding tube. If we now turn to FIG. 2, we can further examine the improved y-port fitting 26 of the present invention.

Figure 2:
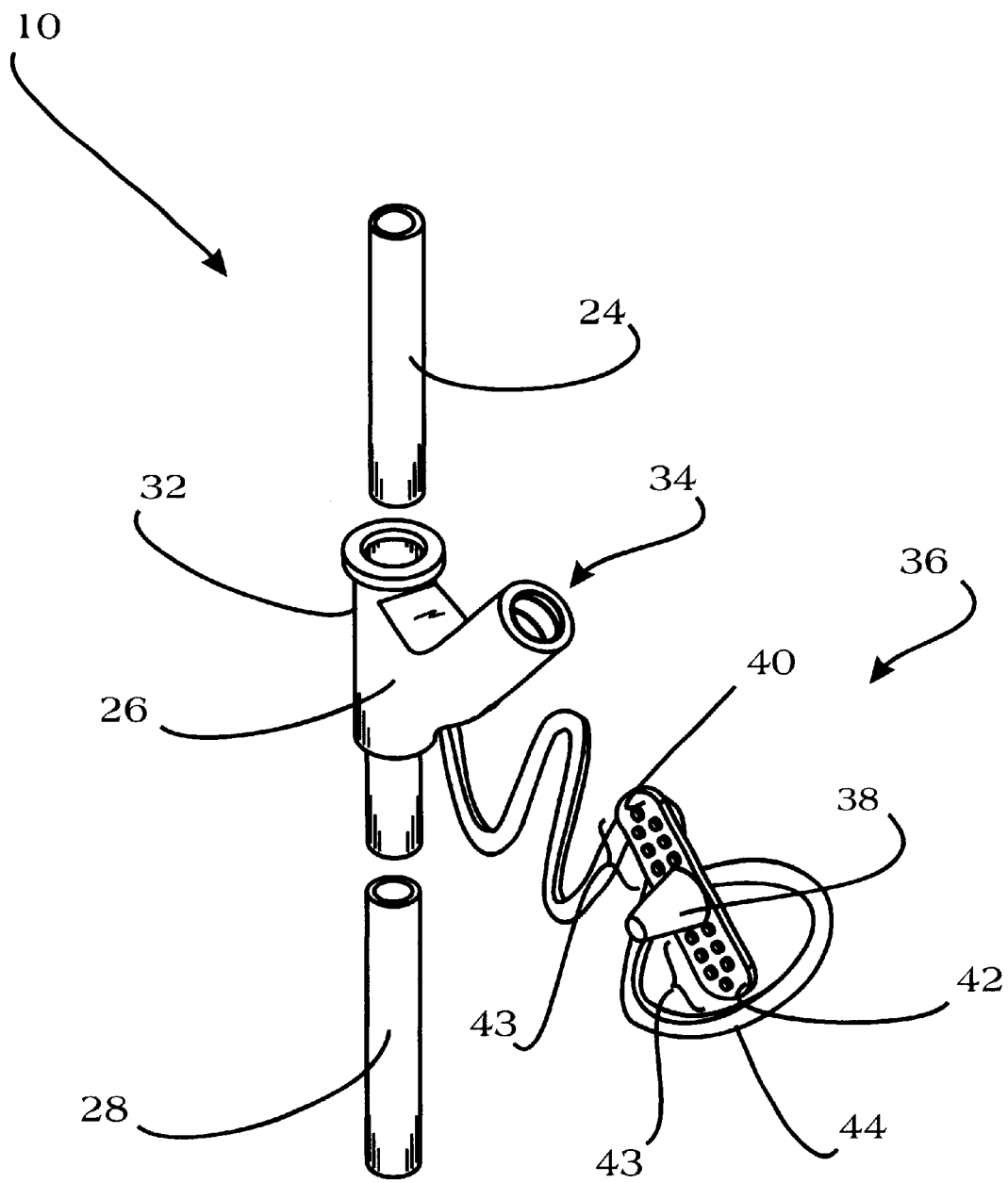
FIG. 2 is a perspective view of the y-port fitting of the spike set of FIG. 1.

FIG. 2 is a perspective view of the y-port fitting 26 of the spike set of FIG. 1. As can be seen in FIG. 2, the y-port fitting 26 comprises a body 32 preferably formed of a non reactive plastic material. Within the body 32 is formed a flushing port 34. Further detail with regard to flushing port 34 will be provided below in connection with other figures. A plug assembly 36 is integral to the fitting 26 in order to permit the port 34 to be sealed when not in use. The plug assembly 36 comprises of a plug 38 and a pair of tabs 40 and 42 to assist in the insertion and removal of a plug 38 to and from the flushing port 34. A plurality of nubs 43 are preferably formed on the surfaces of the tabs 40 and 42 in order to provide additional grip benefits to the user. The plug assembly 36 is attached to the body 32 by a flexible undulating plug retaining member 44. This elongate undulating design is provided to provide additional ease in inserting and removing the plug 38 from the flushing port 34. Furthermore, since the plug retaining member 44 is so long, it will permit healthcare personal to prevent the plug 38 from interfering with their work.

Figure 4:
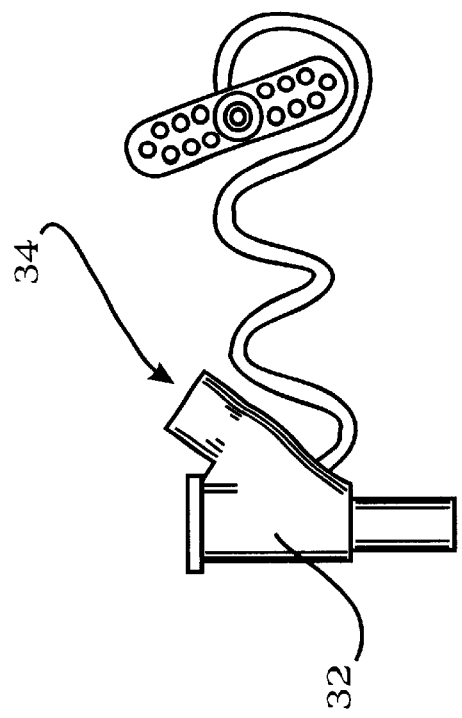
FIG. 4 is a front view of the y-port of FIGS. 1 through 3.
Figure 3:
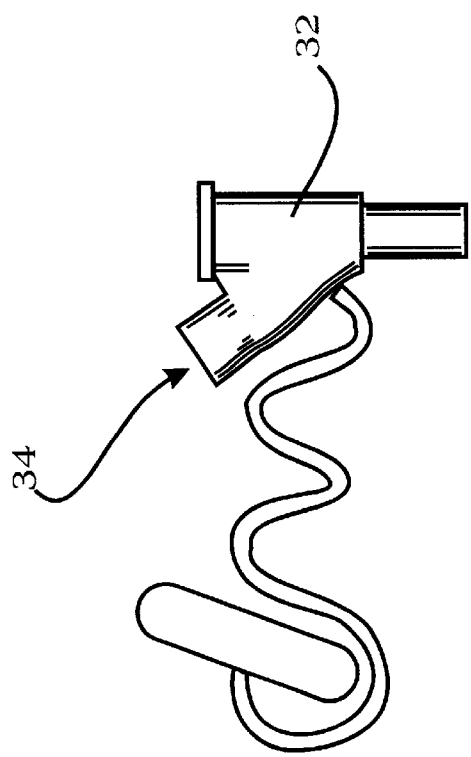
FIG. 3 is a back view of the y-port fitting of FIGS. 1 and 2.

FIGS. 3 and 4 depict back and front views, respectively, of the body 32 and the flushing port 34.

Figure 5:
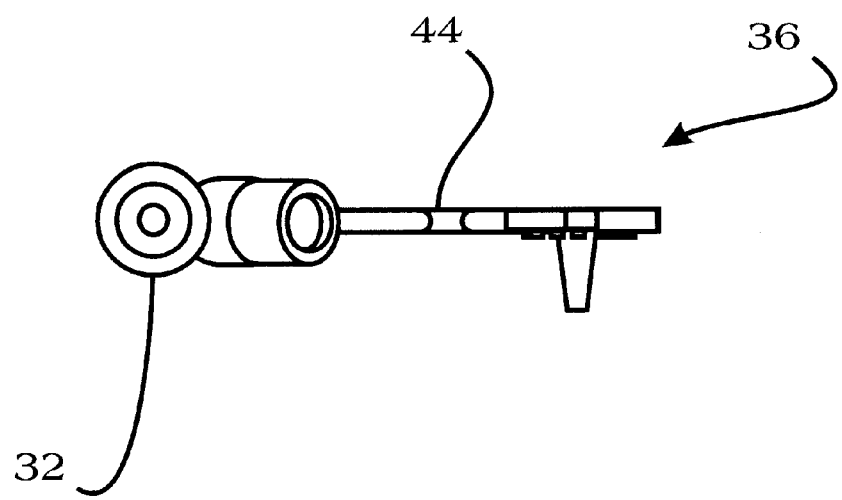
FIG. 5 is a top view of the y-port of FIGS. 1 through 4.
Figure 6:
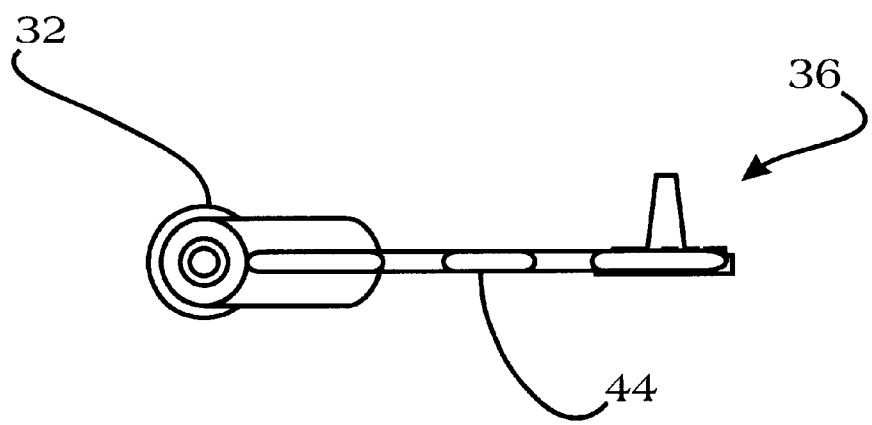
FIG. 6 is a bottom view of the y-port of FIGS. 1 through 5.

FIGS. 5 and 6 depict top and bottom views, respectively, or the plug assembly 36 and the retaining member 44 in the preferred design.

Figure 7:
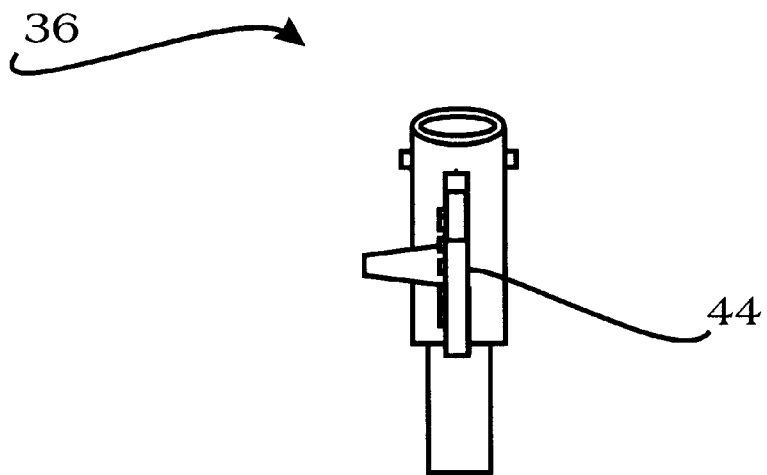
FIG. 7 is a left side view of the y-port of FIGS. 1 through 6.
Figure 8:
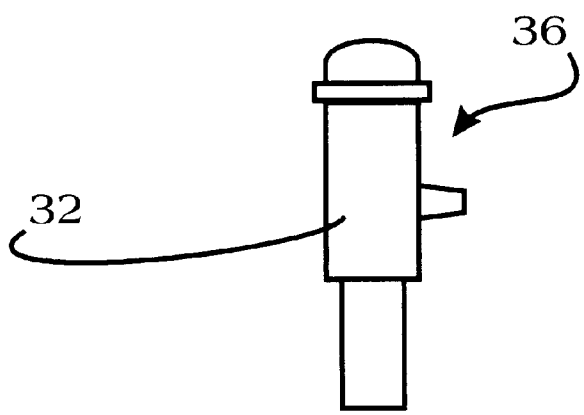
FIG. 8 is a right side view of the y-port of FIGS. 1 through 7.

FIGS. 7 and 8 depict right and left side views of the plug assembly 36, the body 32, and the retaining member 44.

Figure 9:
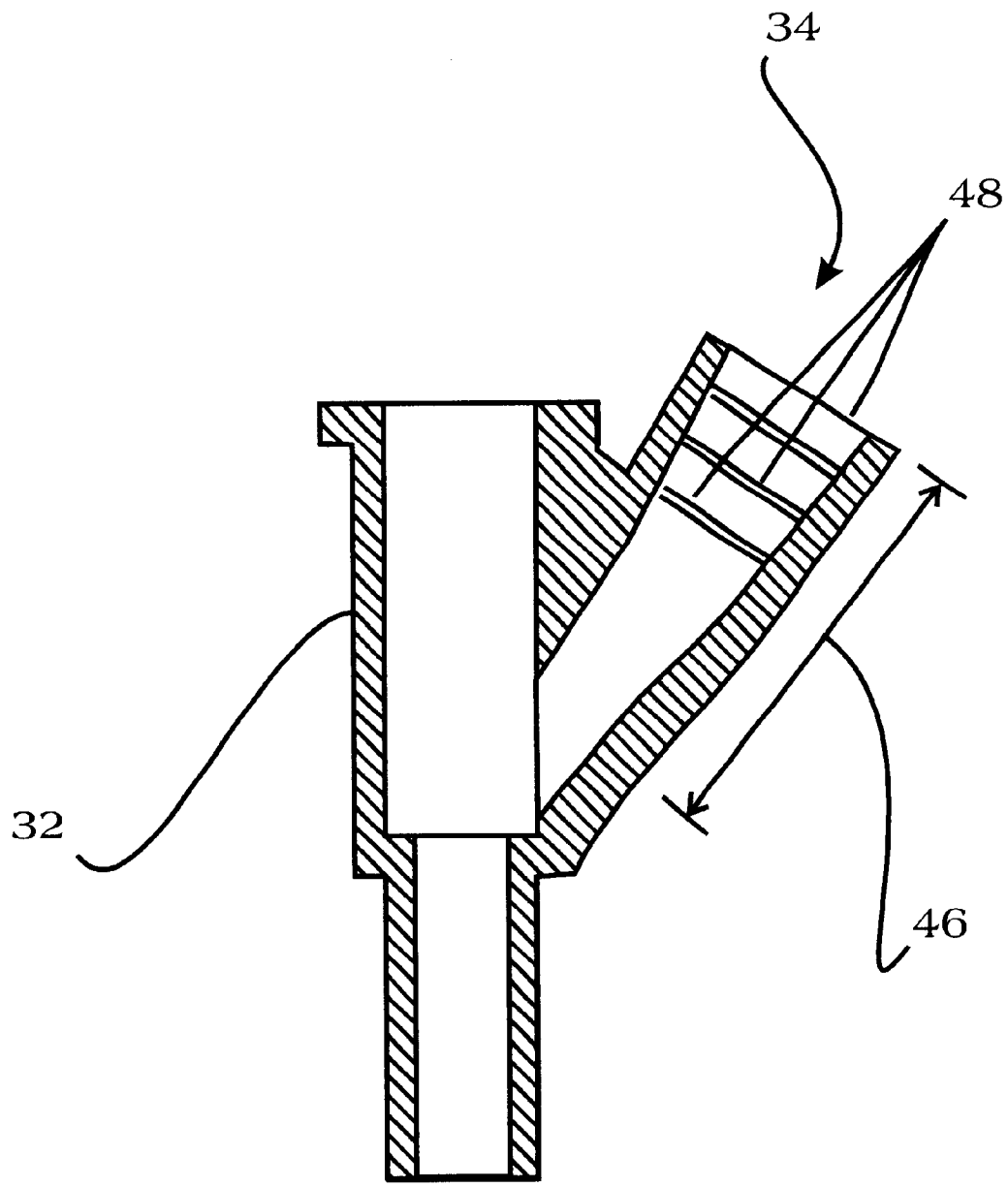
FIG. 9 is a partial cutaway side view of the y-port of FIGS. 1 through 8.

Turning to FIG. 9, we can examine yet another unique feature of the present invention. FIG. 9 is a partial cutaway side view of the y-port 26 of FIGS. 1 through 8. As should be appreciated, the bore depth 46 of the flushing port 34 is longer than the conventional flushing port in order to provide the additional flexibility of using a variety of different syringe tip profiles. Furthermore, along the bore of the flushing port 34 are a plurality of circular ridges 48. These ridges cooperate with the tip of a wide variety of syringes to prevent leakage when water is administered.

Figure 10:
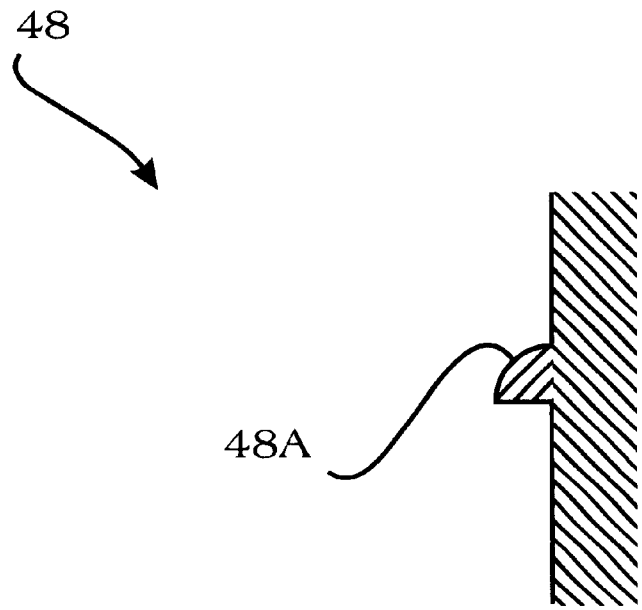
FIG. 10 are partial cutaway side views of preferred ridge designs for the y-port of the present invention.
Figure 10:
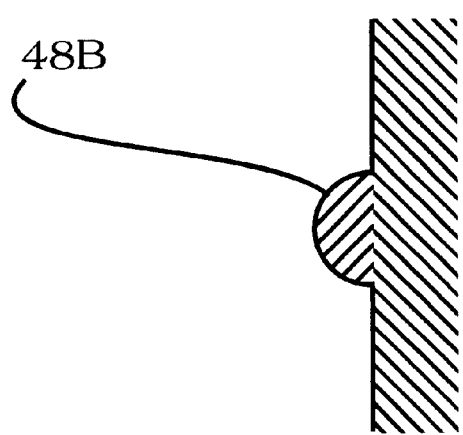

FIG. 10 provides further detail regarding these ridges 48. FIG. 10 are partial cutaway side views of preferred alternate designs for ridges of the present invention. As seen in FIG. 10, the ridges 48, while being circular around the periphery of the flushing port, may have a unique aspect to their cross-section. In one preferred embodiment the ridges will have a non-smooth profile 48A in that the leading edge of the ridge will be smooth, however the trailing edge will be cut off possibly even at a 90-degree or greater angle. This cut-off edge has been seen to provide additional leak prevention in the design by preventing the inserted tip from being removed. In another preferred embodiment a smooth profile ridge 48B will be provided; this ridge, while not providing as substantial of a retaining force upon a syringe that's asserted therein, will likely provide easier engagement and disengagement of the syringe in the flushing port, while still providing substantial leak prevention.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved spike set for enteral feeding, comprising:
   a spike;
   a drip chamber;
   a y-port fitting, said y-port comprising a body defined by a flushing port formed therein, said flushing port defined by a bore having an outer surface, said outer surface including at least one ridge formed thereon;
   a stepped connector; and
   tubing connecting said spike to said drip chamber and said drip chamber to said y-port fitting and said y-port fitting to said stepped connector.

2. The spike set of claim 1, wherein said y-port fitting comprises:
   a retaining member extending from said body, said retaining member defining an undulating shape and having a distal end; and
   a plug assembly at said distal end.

3. The spike set of claim 2, wherein said plug assembly further comprises a plug and a pair of tabs extending therefrom.

4. The spike set of claim 3, wherein said flushing port is configured to receive said plug.

5. The spike set of claim 4, wherein each said ridge defines a semi-circular cross-section.

6. The spike set of claim 4, wherein each said ridge defines a quarter-circular cross-section.

7. The spike set of claim 4, wherein said tabs further include a plurality of nubs formed thereon to provide grip.

8. An improved y-port fitting for eternal feeding, comprising:
   a body flier defined by a flushing port, said flushing port comprising:
      a bore formed in said body,
      said bore further defined by a bore surface, and
      said body further comprising at least one ridge protruding from said bore surface;
   a retaining member extending from said body, said retaining member defining an undulating shape and having a distal end; and
   a plug assembly at said distal end said plug assembly further defined by a plug, said plug configured to be cooperatively accepted in said bore.

9. The y-port fitting of claim 8, wherein said plug assembly further comprises a pair of tabs extending therefrom said plug.

10. The y-port fitting of claim 8, wherein each said ridge defines a semi-circular cross-section.

11. The y-port fining of claim 8, wherein each said ridge defines a quarter-circular cross-section.

12. The y-port fitting of claim 8, wherein said tabs further include a plurality of nubs formed thereon to provide grip.

* * * * *